(12) United States Patent
Matsushita (10) Patent No.: US 7,162,072 B2
(45) Date of Patent: Jan. 9, 2007

(54) SEMICONDUCTOR PROCESSING DEVICE, SEMICONDUCTOR PROCESSING SYSTEM AND SEMICONDUCTOR PROCESSING MANAGEMENT METHOD

(75) Inventor: Hiroshi Matsushita, Fukuoka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 731 days.

(21) Appl. No.: 10/328,937

(22) Filed: Dec. 24, 2002

(65) Prior Publication Data

US 2003/0157736 A1    Aug. 21, 2003

(30) Foreign Application Priority Data

Dec. 25, 2001    (JP)    ............................. 2001-392523

(51) Int. Cl.
  G06K 9/00    (2006.01)
  H04N 7/18    (2006.01)
(52) U.S. Cl. .................. 382/145; 348/86; 348/125; 356/237.1; 438/16
(58) Field of Classification Search ........ 382/145–151; 348/86, 87, 121, 125–134; 356/237.1, 237.6; 438/16
See application file for complete search history.

(56) References Cited

U.S. PATENT DOCUMENTS 4,758,782 A * 7/1988 Kobayashi .................. 382/148

4,977,328 A    12/1990  Van Vucht
6,175,417 B1    1/2001  Do et al.

FOREIGN PATENT DOCUMENTS

| JP | 10-143660 | 5/1996 |
| JP | 11-223662 | 8/1999 |
| JP | 2000-077290 | 3/2000 |

* cited by examiner

Primary Examiner—Jingge Wu
Assistant Examiner—Aaron Carter
(74) Attorney, Agent, or Firm—Hogan & Hartson LLP (57) ABSTRACT

A semiconductor processing device includes a processing section to process a semiconductor substrate in accordance with job information which is used to process the semiconductor substrate. An imaging section takes an image of a processed portion of the semiconductor substrate for each time of processing by the processing section. An image-processing section converts any one and another of the images to image data which are different from each other in data volume, and associates a result of processing from the processing section, the job information and the image data with each other in each processing. An input/output section outputs at least the result of processing and the image data.

18 Claims, 10 Drawing Sheets

SEMICONDUCTOR PROCESSING DEVICE, SEMICONDUCTOR PROCESSING SYSTEM AND SEMICONDUCTOR PROCESSING MANAGEMENT METHOD

CROSS-REFERENCE TO RELATED APPLICATION

This application is based upon and claims the benefit of priority from the prior Japanese Patent Application No. 2001-392523, filed on Dec. 25, 2001, the entire contents of which are incorporated herein by reference.

FIELD OF THE INVENTION

This invention relates to a semiconductor processing device, semiconductor processing system and semiconductor processing management method.

BACKGROUND OF THE INVENTION

Semiconductors generally require many measurement processes for their manufacture. For example, a CD (critical dimension) measurement step for measuring line widths of micro patterns formed on a semiconductor substrate is required for the manufacture of a semiconductor. In CD measurement, line widths of a resist pattern used in a photolithographic step, line widths of wirings and trench widths or trench widths formed in an etching step, and so on, are measured. A CD measuring device measures portions of a semiconductor substrate with electron beams while monitoring them in an enlarged scale.

The image of a certain measuring portion, which is monitored by a CD measure, is typically used for analysis of defects. For analysis of defects, the image is digitally converted and stored as image data. To find causes of the defects early, it is desirable that the image data is of a high quality.

However, the higher the quality of the image data, the larger the volume of the image data. In case the volume of the image data is large, it takes a long time to digitally convert, input or output the image data, write or read the image data, and so forth. As a result, semiconductor processing devices such as CD measures take a long time to process the semiconductor substrate. This means that semiconductor processing devices degrade in throughput. This results in increasing the cycle time of the semiconductor manufacturing process and hence increasing the manufacturing cost of semiconductor elements.

Figure 11:
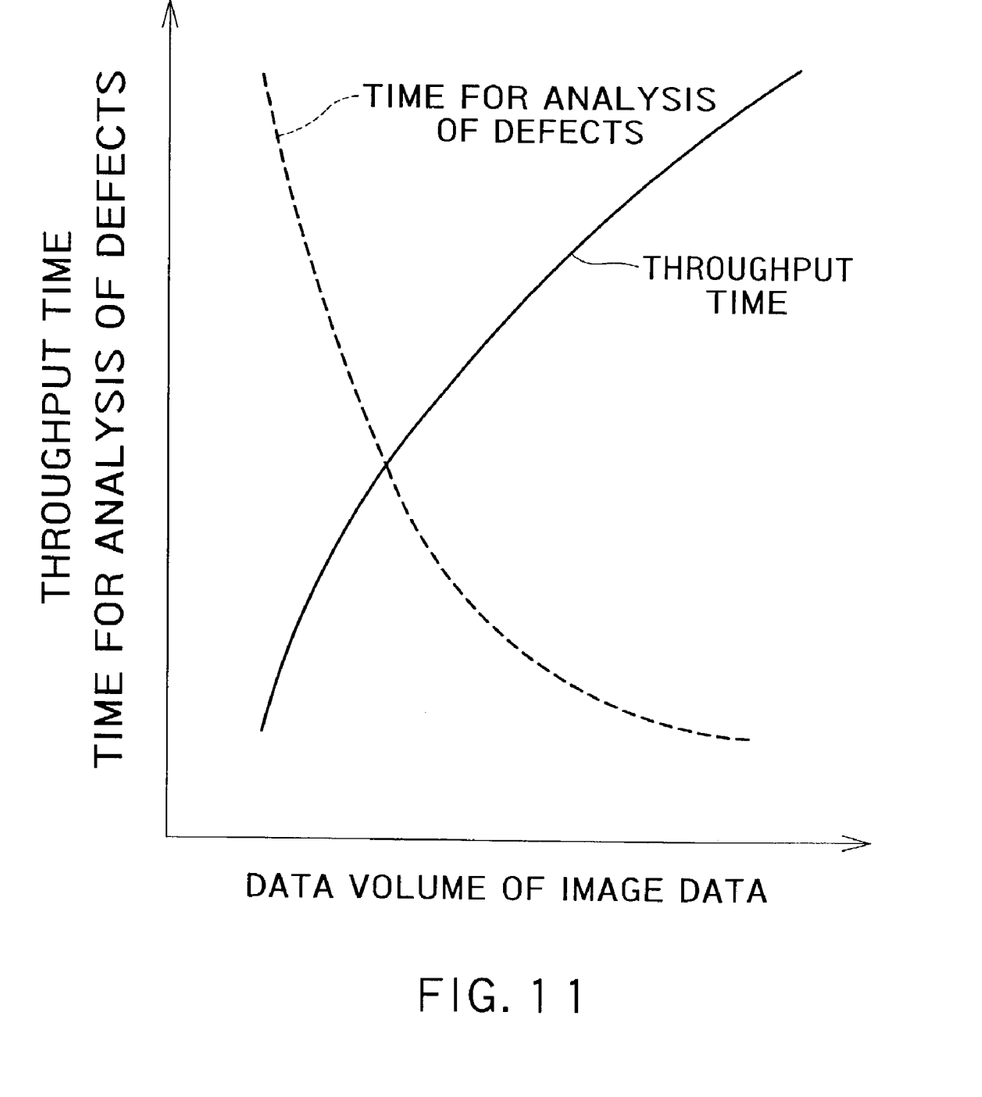
FIG. 11 is a graph that shows throughput time of the semiconductor processing device and time required for analysis of defects relative to volume of image data in a conventional technique.

FIG. 11 shows a graph that exhibits changes of the throughput of a semiconductor processing device and the time for analysis of defects relative to volumes of image data. FIG. 11 shows such changes schematically for better understanding.

According to FIG. 11, the larger the volume of image data, the higher the quality of the image and the shorter the time required for analysis of its defects. On the other hand, the larger the volume of the image data, the longer the throughput time of the semiconductor processing device.

That is, there is a trade off between the time required for analysis of defects and the throughput of the semiconductor processing device in relation to the volume of the image data. It is needed to digitally convert individual images to image data files that are different from each other in terms of data volume or file format in order to attain equilibrium between the time required for analysis of defects and the throughput time of the semiconductor processing device.

In general, the measuring condition in CD measurement includes information about the data volume of image data upon digital conversion. Therefore, the measuring condition must be modified to change the information about the data volume of the image data.

However, after executing measurement according to a certain measurement condition, it is difficult and troublesome to continue the measurement by changing the file format in the measuring condition and the data volume.

Conventionally, therefore, it was difficult to digitally convert individual images to image data files different from each other in data volume or file format.

Under the circumstances, there is a demand for a semiconductor processing device, semiconductor processing system and semiconductor processing management method capable of digitally converting individual images to image data files different from each other in volume or file format.

SUMMARY OF THE INVENTION

A semiconductor processing device according to an embodiment of the invention comprises:

a processing section to process a semiconductor substrate in accordance with job information which is used to process the semiconductor substrate;

an imaging section to take an image of a processed portion of the semiconductor substrate upon each time of processing by said processing section;

an image-processing section to convert any one and another of said images to image data which are different from each other in data volume, and to associate a result of processing from the processing section, said job information and said image data with each other in each processing; and an input/output section capable of outputting at least the result of processing and the image data.

A semiconductor processing system according to an embodiment of the invention comprises:

(a) a semiconductor processing device comprising:
  a processing section to process a semiconductor substrate in accordance with job information which is used to process the semiconductor substrate;
  a imaging section to take an image of a processed portion of the semiconductor substrate upon each time of processing by said processing section;
  an image-processing section to convert any one and another of said images to image data which are different from each other in data volume, and to associate a result of processing from the processing section, said job information and said image data with each other in each processing; and
  an input/output section capable of outputting at least the result of processing and the image data, and (b) a host computer being connected to the semiconductor processing device to input and store at least the result of processing and the image data which are output from the input/output section.

A semiconductor processing management method according to an embodiment of the invention for use with a semiconductor processing device, which includes a processing section to process a semiconductor substrate, a imaging section to take an image of the semiconductor substrate upon processing by the processing section, and an image-processing section to process the image, comprises:

processing the semiconductor substrate according to job information which is prepared for processing the semiconductor substrate;

taking an image of the semiconductor substrate upon each time of processing by the processing section;

converting any and another of the images to image data which are different from each other in data volume;

associating the result of processing from the processing section, the job information and the image data with each other; and externally outputting at least the result of processing and the image data.

DETAILED DESCRIPTION OF THE INVENTION

Embodiments of the invention are explained below with reference to the drawings. The embodiments, however, should not be construed as any constraint on the scope of the invention.

Figure 1:
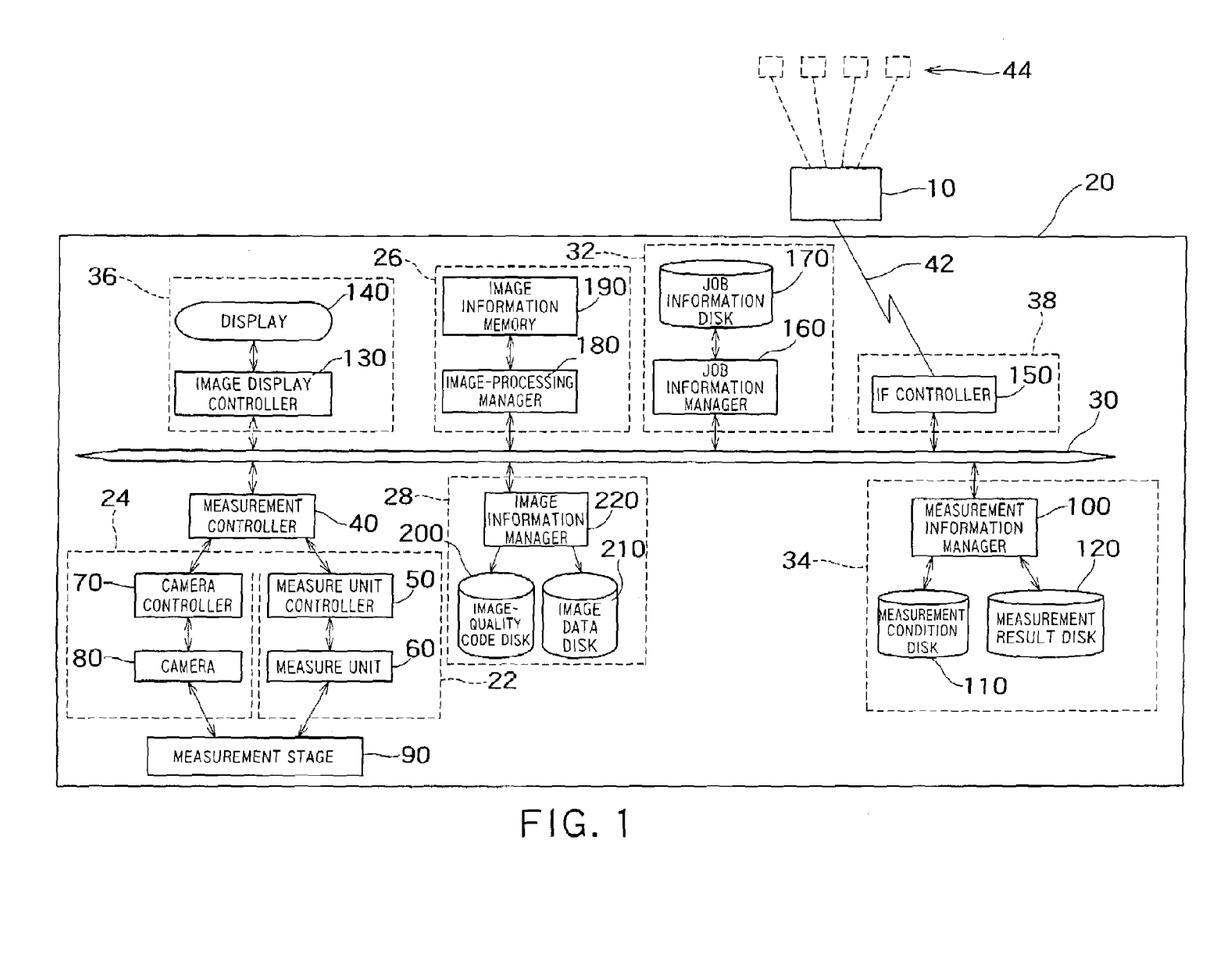
FIG. 1 is a block diagram that shows the outline of a semiconductor processing device according to an embodiment of the invention.

FIG. 1 is a block diagram that shows the outline of a semiconductor processing device 20 according to an embodiment of the invention.

The semiconductor processing device 20 shown here measures a pattern formed on a semiconductor substrate (not shown) which is placed on a measurement stage 90. The semiconductor processing device 20 makes an image of a measured point of the semiconductor substrate simultaneously with the measurement.

In particular, the semiconductor processing device 20 includes a measure section 22 for measuring a pattern formed on the semiconductor substrate according to a measurement condition. The measure section 22 includes a measure unit 60 for measuring the semiconductor substrate and a measure unit controller 50 for controlling the measure unit 60.

The semiconductor processing device 20 further includes a imaging section 24 for making an image of a measured point on the semiconductor substrate upon the measurement by the measure section 22. The imaging section 24 includes a camera 80 for making an image of the measured point, and a camera controller 70 for controlling the camera 80. The semiconductor processing device 20 also includes a measurement controller 40 for controlling the measure section 22 and the imaging section 24.

The image made by the imaging section 24 may be either a static image or a moving image. The image made by the imaging section 24 may be either a color image or a monochromatic image. In case a high quality image is preferred regardless of its larger volume of image data, a moving image or a color image may be employed. In case a smaller volume of image data is preferred regardless of a lower quality of the image, a static image or a monochromatic image may be employed.

The semiconductor processing device 20 also includes an image-processing section 26 and an image storage section 28. The image-processing section 26 includes an image-processing manager 180 for processing the image made by the imaging section 24, and image information memory 190 that can store selection information. The image-processing manager 180 digitally converts the image to image data. Additionally, the image-processing manager 180 associates a result of the measurement from the measure section 22 with the image made by the imaging section 24.

The image storage section 28 includes an image-quality disk 200 for storing image codes containing information about the data volume of image data, file format, and so on; image data disk 210 for storing image data digitally converted by the image-processing section 26; and image information manager 220 for managing the image-quality code disk 200 and the image data disk 210. The image information manager 220 writes an image-quality code on the image-quality code disk 200 or reads it from the disk 200. Additionally, the image information manager 220 writes image data on the image data disk 210 or reads the data from the disk 210.

The semiconductor processing device 20 further includes a job information storage section 32 and a result-information storage section 34. The job information storage section 32 includes a job information disk 170 for storing job information and a job information manager 160 for writing job information on the job information disk 170 or reading out the information from the disk 170. The job information specifies a semiconductor substrate to be measured and/or a point thereof to be measured, and specifies a condition for the measurement.

The result-information storage section 34 includes a measurement condition disk 110 for storing the condition for the measurement, measurement result disk 120 for storing the result of the measurement, and measurement information manager 100 for managing the measurement condition disk 110 and the measurement result disk 120. The measurement information manager 100 writes the result of the measurement on the measurement result disk 120 or reads it out of the disk 120. Additionally, the measurement information manager 100 reads the measurement condition from the measurement condition disk 110 or writes it on the disk 110.

The image-quality code disk 200 is prepared independently from the measurement condition disk 110 and the job information disk 170. Therefore, the semiconductor processing device 20 can change the data volume of any image data only by changing the information about the data volume in the image-quality codes without changing the job information and/or measurement condition.

The semiconductor processing device 20 further includes a monitor section 36. The monitor section 36 includes a display 140 capable of outputting job information, measurement condition, measurement result, image-quality code or image, and an image display controller 130 for controlling the display 140.

An input/output section 38 connects the semiconductor processing device 20 to a host computer 10 outside the semiconductor processing device 20 via an interface 42. The input/output section 38 has an IF controller 150 for controlling the interface 42, and makes it possible to output a result of the processing and image data associated with each other to the host computer 10.

Those and other components of the semiconductor processing device 20 shown here are connected together by lines 30 inside of the device 20 as shown in FIG. 1.

However, all or part of the components of the semiconductor processing device 20 may be placed in the host computer 10. Alternatively, all or part of the components of the semiconductor processing device 20 may be outside of the device 20 and connected together to form a semiconductor processing network. In this case, the semiconductor processing device 20 can be reduced in size (capacity) and/or area for its installation, and there is more freedom of choice in its placement.

Alternatively, without using the host computer 10, all of job information, image data, measurement results, and so on, may be stored in the semiconductor processing device 20 such that connection to exterior devices is not required.

The semiconductor processing device 20 may be a semiconductor inspection device for measuring line widths of patterns formed on the semiconductor substrate. However, it may be a semiconductor manufacturing device incorporating the components shown in FIG. 1, such as a projection aligner or etcher, for example.

In the instant embodiment, the host computer 10 previously stores selection information for determining which of the image-quality codes should be selected. The selection information can be easily rewritten by access to the host computer 10. Additionally, the host computer 10 stores job information, image data and measurement results input from the input/output section 38.

A file server or a database server can be used as the host computer 10. The system may be configured such that any client 44 can be connected to the file server or database server. Such a client-server type semiconductor processing system makes management of the semiconductor processing device 20 easier.

The network, semiconductor processing system or interface 42 may use any of electric communication and optical communication from the viewpoint of the speed of communication, and may use any wired and wireless communication taking into account the spatial condition for installation and transmission distance of the site for its installation.

The image data upon measurement may be transmitted sequentially also to the host computer 10 through the input/output section 42 in addition to the monitor section 36 such that the state of measurement can be monitored outside the semiconductor processing device 20 as well at any time.

Figure 2:
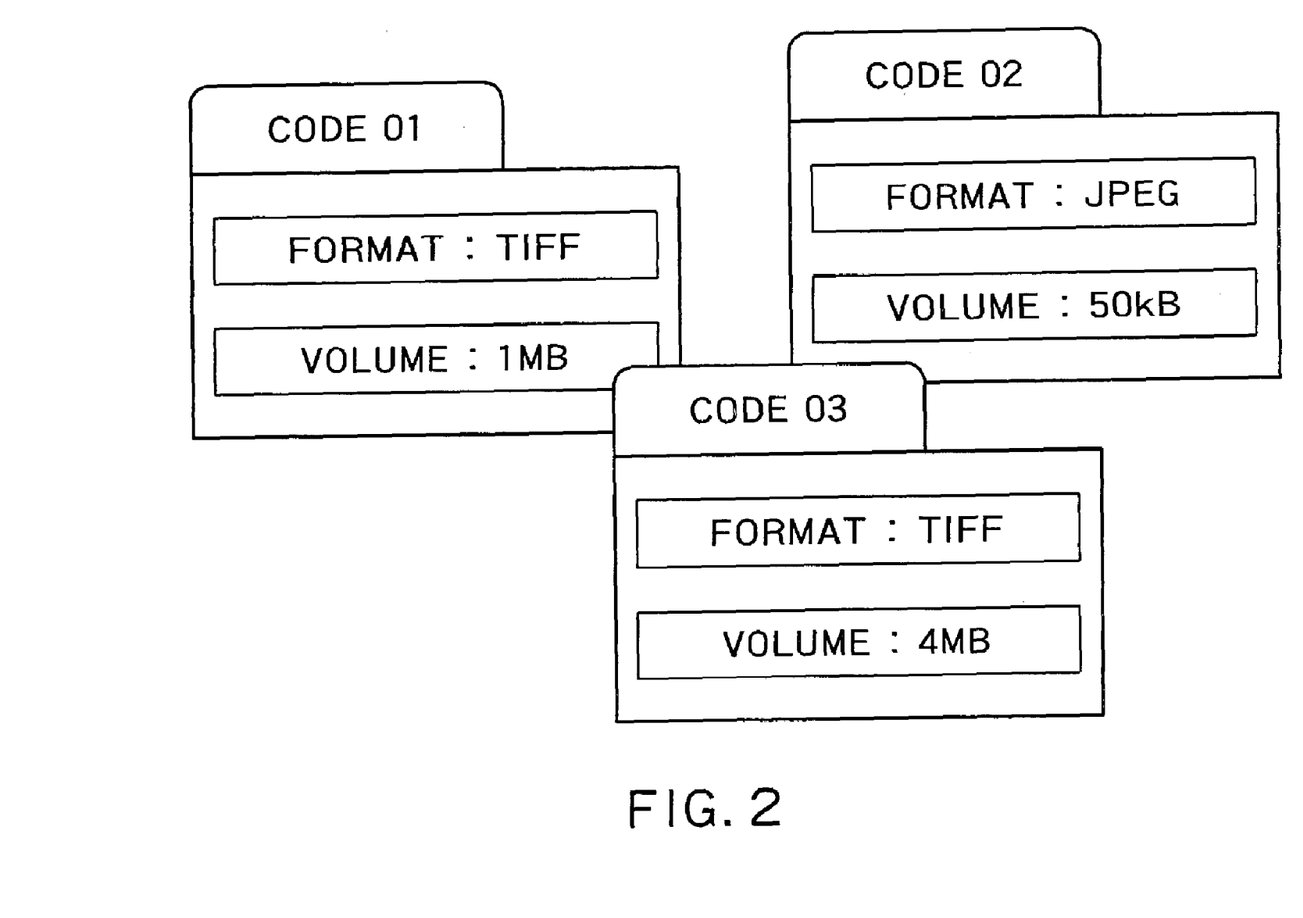
FIG. 2 is a diagram that conceptually shows image-quality codes.

FIG. 2 is a diagram that conceptually shows image-quality codes. Three image-quality codes are shown here. The image-quality codes are different from each other in the information they have. In the embodiment shown here, the image-quality codes have information about different file formats or information about data volumes different from each other.

In greater detail, the image-quality code 01 contains TIFF (Tagged Image File Format) as the information about the file format and 1 MB (megabytes) as the information about the data volume. The image-quality code 02 contains JPEG (Joint Photographic Experts Group) as the information about the file format and 50 kB (kilobytes) as the information about the data volume. The image-quality code 03 contains TIFF as the information about the file format and 4 MB as the information about the data volume. The file formats may be BMP (Bit Map), PICT (Macintosh Picture), RAS (Sun Rasfilter Format), or the like.

Any image requiring conversion to high image quality data among images stored in the image information storage memory 190 is digitally converted according to the image-quality code 03, for example. In case of an image for which conversion to a low image-quality data is sufficient, it is digitally converted according to the image-quality code 02.

If the image needs conversion to high image quality data, it may be stored as the analog signal in the image data disk 210 without digital conversion. As a result, a higher quality image can be obtained. The image-quality codes may contain information about compression ratios of image data instead of data volumes or in addition to data volumes.

In case the image is a moving image, MPEG (Moving Picture Experts Group) is employed in lieu of JPEG or TIFF. This format makes it possible to convert not only still images but also moving images to image data of any data volume.

The number of image-quality code may be only two, or more than three. Additionally, each image-quality code may contain identification of products or processes to which the image-quality code is employed, or may contain identification of administrators of the products and processes, thereby to make management of image-quality codes easier.

Figure 3:
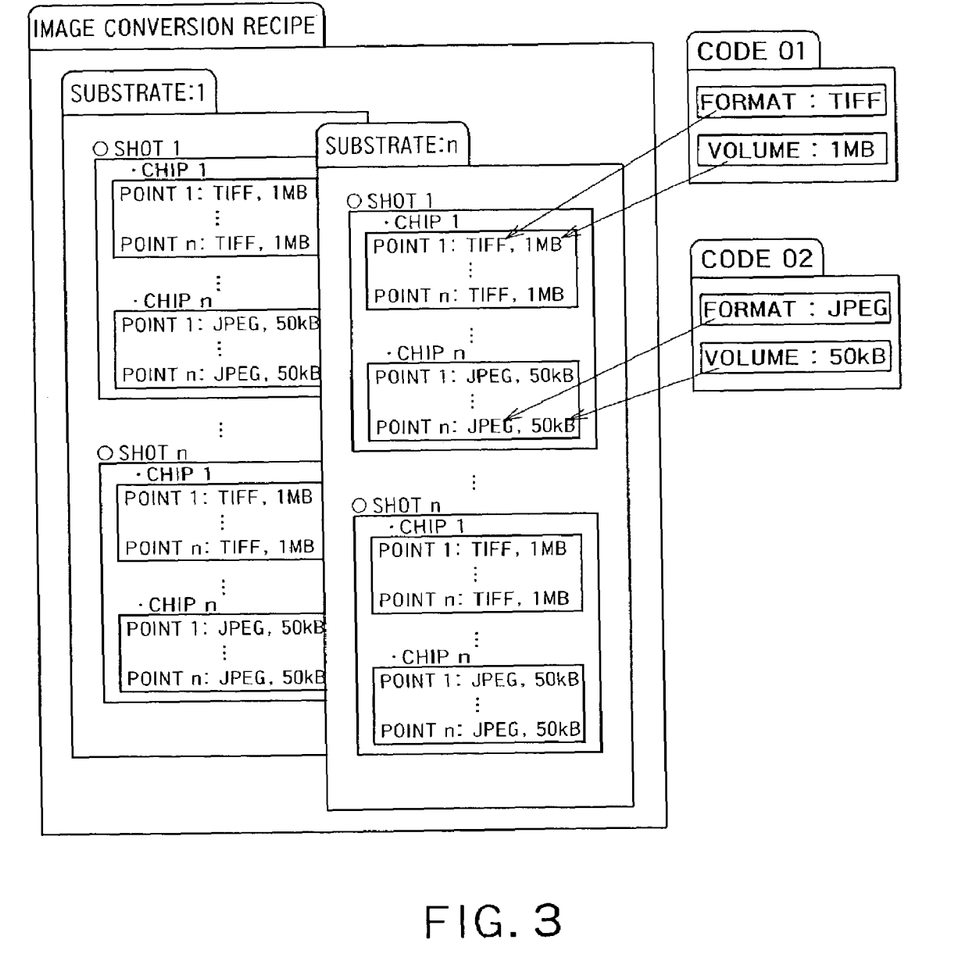
FIG. 3 is a diagram that conceptually shows a process of selecting image-quality codes for respective images.

FIG. 3 is a diagram that conceptually shows a process of selecting image-quality codes for respective images. The image-processing controller 180 selects the appropriate image-quality code according to the selection information input from the host computer 10. As a result, a series of image conversion recipe indicating which of the image-quality codes should be employed for digital conversion of each image is formed.

According to the instant embodiment, the semiconductor processing device 20 measures line widths of a photo resist patterned in a photolithographic process, and the imaging section 24 makes an image of each measured point during each measurement.

In the embodiment shown here, the image conversion recipe is prepared for each semiconductor substrate. Then the image-quality code 02 is selected for a chip at a position in a shot by the projection aligner, and the image-quality code 01 is selected for other chips.

For example, images of chips in a location of a semiconductor substrate exhibiting a statistically high fraction defective are stored in a high image quality to facilitate analysis of defects and to reduce the time for the analysis. In contrast, images of chips in a location of the semiconductor substrate exhibiting a statistically low fraction defective are stored in a lower image quality. In this case, since the data volume of the image data is smaller, the time required for input or output of the image data is shortened.

Therefore, the trade-off relationship between the time for analysis of defects and the throughput time of the semiconductor processing device is removed.

In the instant embodiment, limited chips in a predetermined location within a shot of the projection aligner are processed by an image-quality code different from those of other chips. However, it is not indispensable to select different image-quality codes for respective chips.

Figure 4:
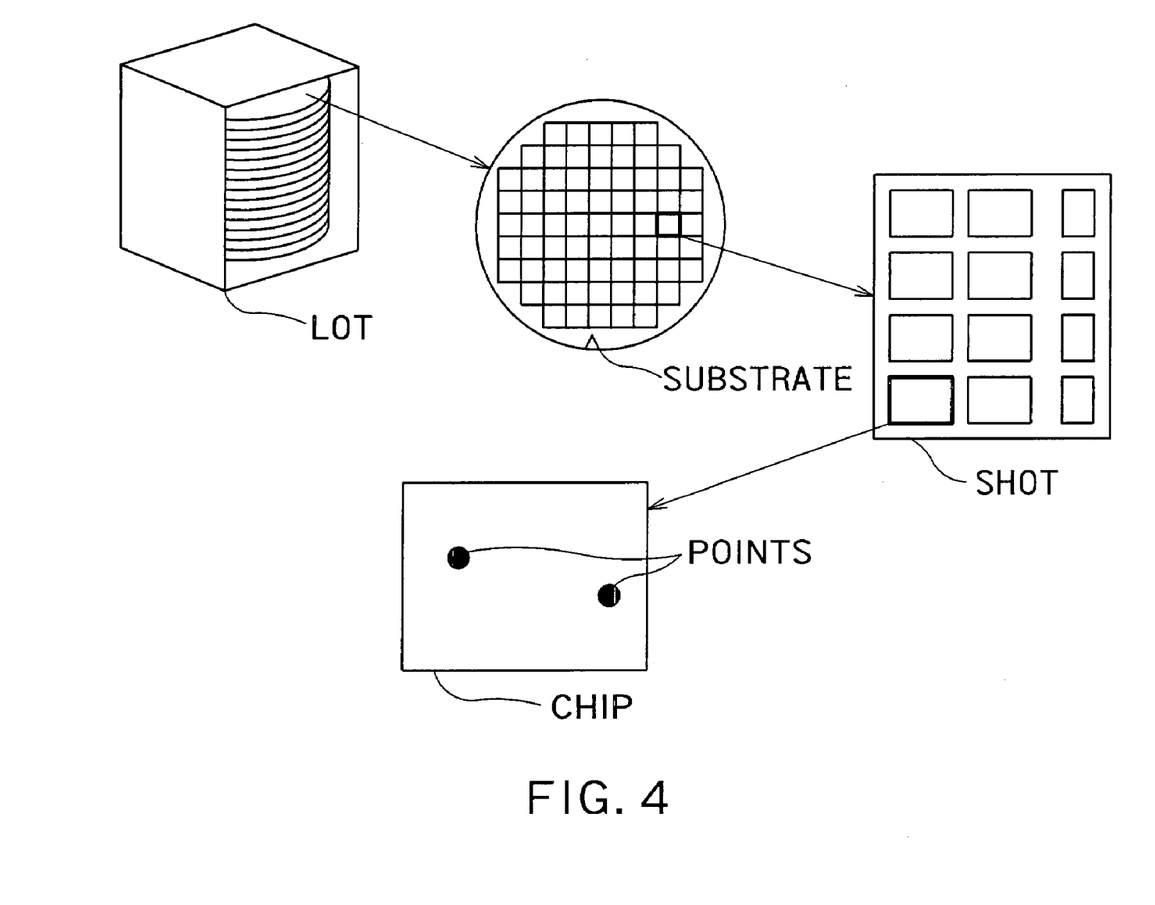
FIG. 4 is a diagram that shows a process where an image-quality code is being selected.

As shown in FIG. 4, a single image-quality code may be selected for all chips in each lot, for example, or for all chips on each semiconductor substrate. Further, a single image-quality code may be selected for each shot of the projection aligner, or different image-quality codes may be selected for individual points for measurement within a single chip.

It is also acceptable to select an image-quality code for each group of a predetermined number of images which is different from those of other groups of images. It is also acceptable to process an image selected at random with an image-quality code different from those of other images.

Next explained is a method of managing semiconductor processing.

Figure 5:
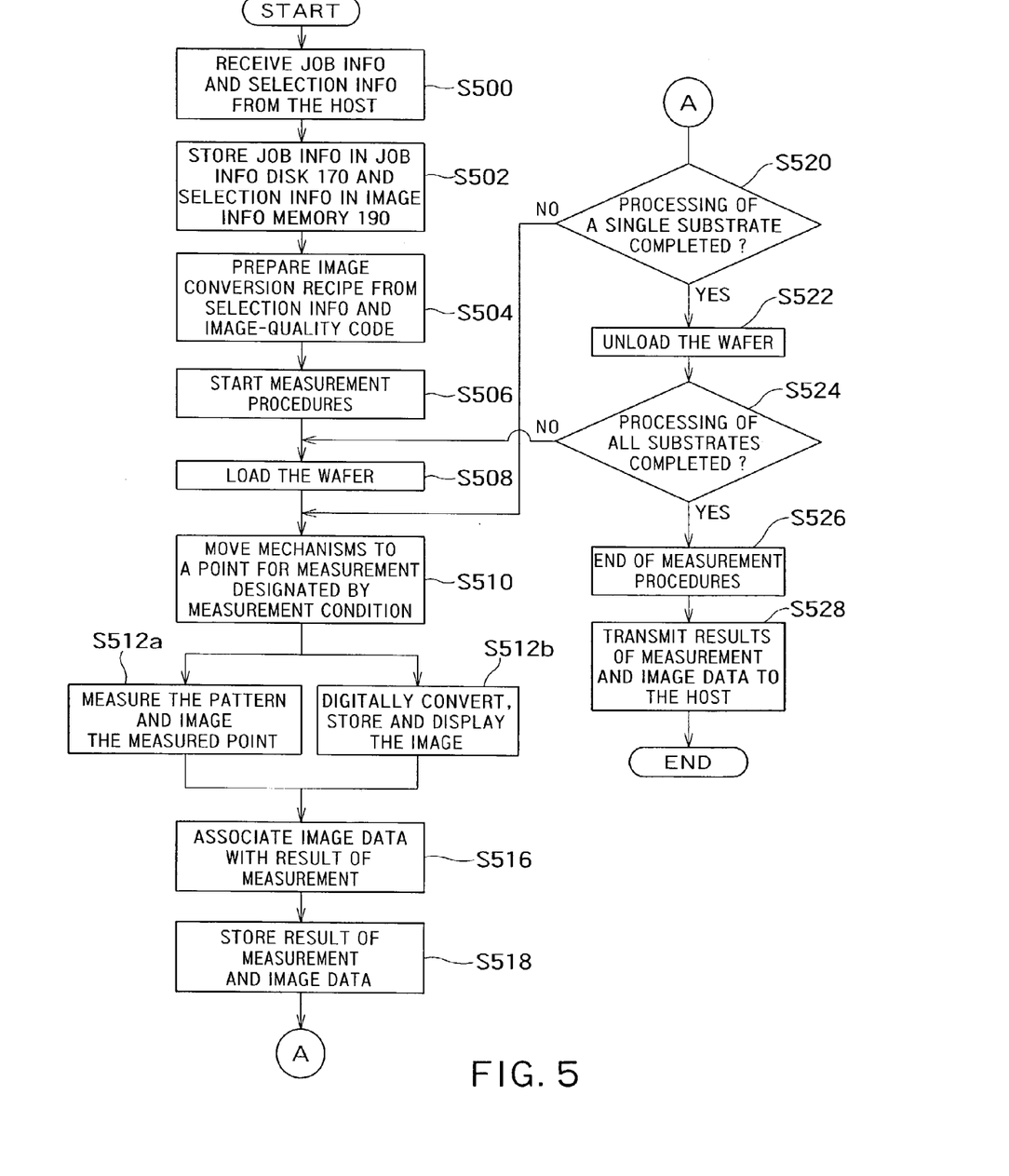
FIG. 5 is a flowchart that shows a semiconductor processing management method according to a further embodiment of the invention.

FIG. 5 is a flowchart that shows a semiconductor processing management method according to an embodiment of the invention. The semiconductor processing device 20 receives job information and selection information from the host computer 10.

The job information is sent to the job information storage section 28 and stored in the job information disk 170. The selection information is sent to the image-processing controller 180 and stored in the image information storage memory 190 (S502).

The image information controller 180 next receives image-quality codes, which correspond to individual points for measurement, from the image-quality code disk 200 through the image-quality information manager 220 according to the selection information. The image-quality information controller 180 then allocates the image-quality codes, which are selected for respective points for measurement, according to the selection information, and makes an image conversion recipe (S504). The image conversion recipe is data in the form of an array of image-quality codes that may be arranged in the order of the imaging sequence.

In the next step, the job information manager 160 extracts a measurement condition from the measurement condition disk 110 according to the job information, and sends the measurement condition to the measurement controller 40. The measurement controller 40 starts measurement procedures according to the measurement condition (S506).

First, a semiconductor substrate to be processed is loaded from a lot corresponding to the lot number contained in the job information (S508). Then the measurement stage 90 moves the semiconductor substrate such that the measure unit 60 and the camera 80 come to a position specified by the measurement condition (S510).

After that, the measure unit 60 measures the pattern on the semiconductor substrate, and simultaneously, the camera 80 takes a picture of the measured point on the semiconductor substrate (S512a).

In greater detail, in the process of CD measurement of the pattern on the semiconductor substrate, the measure section 22 measures the width of the pattern formed on the semiconductor substrate. For example, line width of a patterned resist, line width of an etched wiring, width of an etched trench, or the like is measured. The camera 80 takes a picture of the measured point upon being focused to the measured point during the measuring procedure.

The imaging section 24 is typically a scanning electron microscope (SEM) used for CD measurement. The imaging section 24 may be an optical microscope or transmission electron microscope (TEM).

The measure section 22 may measure the width of a region of a pattern formed in a flat shape from different materials. In this case, the measure section 22 measures the width of the region by detecting reflected light caused by the difference in color or material in the pattern when it is focused. In this case, the measure section 22 can measure not only the line width of a wiring or the trench width, but also the width of a region of a flat pattern.

While the measure section 22 and the imaging section 24 engage in measuring and taking an image procedures of the pattern, the measurement controller 40 successively sends the images to the image-processing controller 180 and its monitor section 36. The image-processing controller 180 digitally converts the images according to the image conversion recipe. For example, the images are compressed according to JPEG or TIFF format (S512b).

The digitally converted image data are stored in the image information memory 190. The monitor section 36 displays the image on the display 140 under the control of the image display controller 130 (S512b).

The image-processing controller 180 receives the result of the processing, job information and image data, and gives them a common file name. The job information, image data and measurement result upon measurement of a certain measured point are associated with each other by having the common file name. Therefore, the job information, image data and measurement result can be specified for which measured point they were obtained by measurement even if they are stored separately.

As the file name, an operator may input the lot number, wafer number measurement coordinates, etc. Preferably, however, the image-processing controller 180 automatically writes the day and time of measurement as the file name. If the file name is the day and time of measurement, data up to the year, month, day, hour, minute and second make it possible to specify to which measured point a certain image data corresponds, and thereby saves the operator's work of inputting the file name.

On the other hand, job information, image data and measurement result which are obtained by measurement of a common point are distinguished from each other by using different file formats for job information, image data and result of measurement, for example, by using different extensions of files. Distinction may be also possible by using different directories for storing these types of information, respectively.

In this manner, the job information, image data and measurement result obtained by measurement of a common point are associated with each other (S516).

The image data are next stored in the image data disk 210. The measurement result is stored in the measurement result disk 120 (S518).

After completing measurement procedures of a certain point, if any other point on the semiconductor substrate to be measured is not measured yet, the steps from S510 to S518 are repeated for the point to be measured (S520).

When measurement of all measured points on a semiconductor substrate to be measured is completed, the semiconductor substrate is unloaded from the measurement stage 90 (S522).

Then another semiconductor substrate to be measured is loaded on the measurement stage 90, and the steps from S508 to 522 are repeated (S524).

After completion of the processing of the semiconductor substrate, if no semiconductor substrate remains unprocessed in the lot to be measured, the measurement procedures end (S526).

Once the measurement procedures end, the job information manager 160 transmits the job information, image data and measurement results from the measurement result disk 110 through the IF controller 150 and the interface 42 to the host computer 10 (S528). The host computer 10 inputs and stores the results of the processing and image data output from the IF controller 150.

After completing the processing of a certain lot, processing of the next lot is started.

The image conversion recipe is used upon digital conversion of the image. Therefore, its preparation (S504) may be executed any time from START to S512b.

Digital conversion of the image (S512b) may be executed any time after taking an image of the measured point (S512a) and before transmission of the image data to the host computer 10 (S528). For example, the image data disk 210 stores the image in the form of the analog signal until completion of the measurement procedures (S526). After completion of the measurement procedures (S526), the image-processing controller 180 digitally converts all images in storage in the image data disk 210 collectively.

In this embodiment, any image can be converted to high image quality data having a relatively large data volume. High image quality data are useful for analysis of defects and assurance of reliability. Other images are converted to lower-quality images having a relatively small data volume to reduce the time for input/output and the time for storage of the image data. Therefore,here the trade-off relationship between the time for analysis of defects and the throughput time of the semiconductor processing device is removed.

The greater the number of image codes, the greater the number of image data file types different in data volume and file format. By using many image codes, image data of any desired data volume can be obtained.

Figure 6:
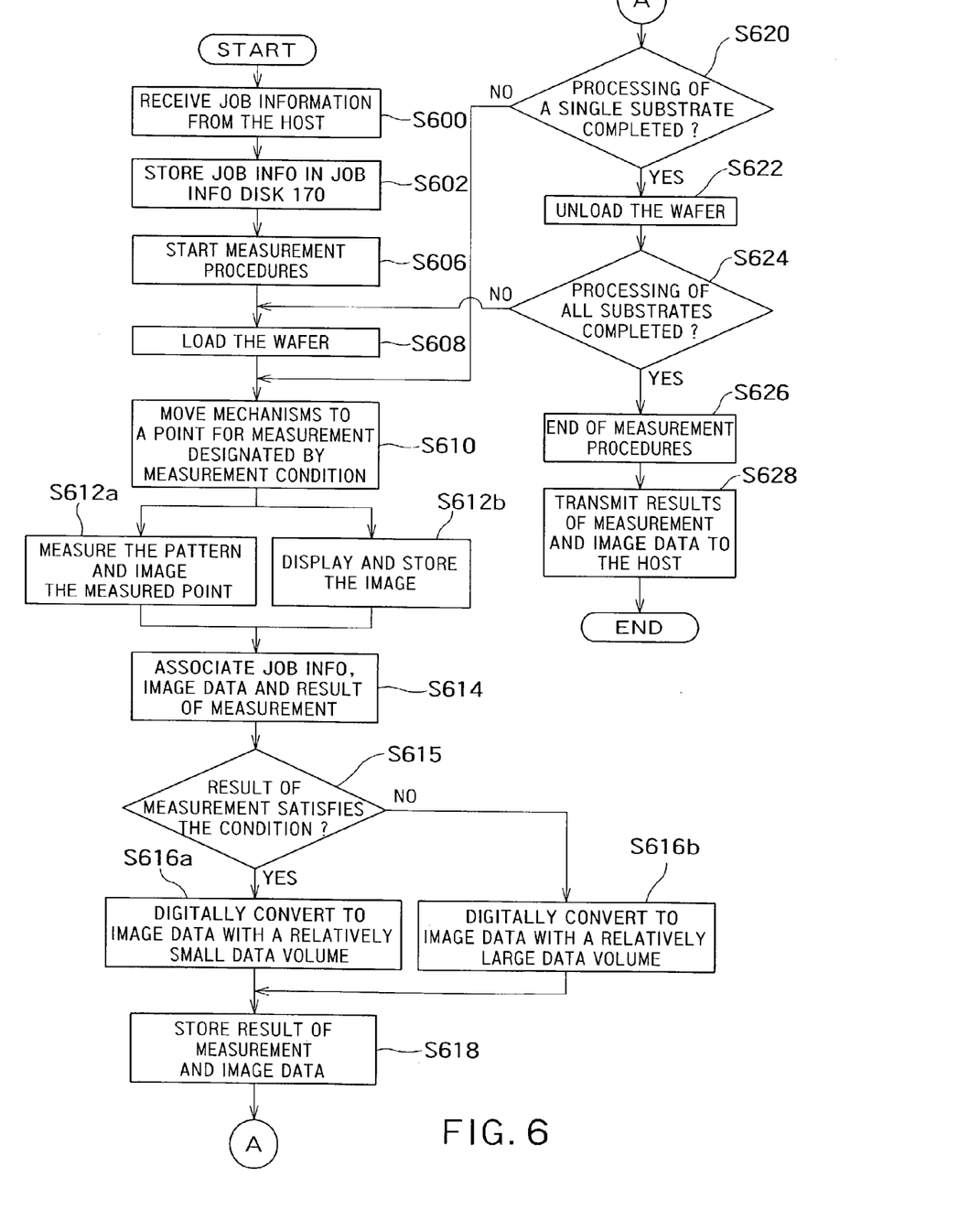
FIG. 6 is a flowchart that shows a semiconductor processing management method according to a further embodiment of the invention.

FIG. 6 is a flowchart that shows a semiconductor processing management method according to a further embodiment of the invention. This embodiment is similar to the embodiment shown in FIG. 5, and the only different features are explained below. In this embodiment, unlike the embodiment of FIG. 5, the image-processing controller 180 judges whether the result of measurement satisfies a predetermined condition (S615). Depending on the result of the judgment, an image code is selected.

In case the result of measurement is a normal result of measurement satisfying the predetermined condition, the image may be relatively low in quality, and, a low image-quality code is selected. The value of the data volume corresponding to the low image-quality code is small. Therefore, the image-processing controller 180 digitally converts the image to image data with a relatively low data volume (S616a).

In contrast, in case the result of measurement is an abnormal result of measurement not satisfying the predetermined condition, the image must be relatively high in quality, and a high image-quality code is selected. The value of the data volume corresponding to the high image-quality code is large. Therefore,the image-processing controller 180 digitally converts the image to image data with a relatively large data volume (S616b).

As a result, since the image data associated with normal one of the results of measurement has a small data volume, the time for read and write of the image data or transmission thereof is shortened. On the other hand, since the data associated with an abnormal result of measurement has a large data volume, a high image-quality can be reproduced. Thereby, analysis of the defects becomes easier, and it is possible to shorten the time for analysis of the defects.

Therefore, the trade-off relationship between the time for analysis of defects and the throughput time of the semiconductor processing device is removed.

Additionally, the instant embodiment, unlike the embodiment of FIG. 5, does not require the image conversion recipe and selection information. As a result, operators need not set the selection information and need not input this information into the host computer. That is, in the instant embodiment, an image code is automatically set in accordance with the result of the judgment.

The image-processing controller 180 may be alternatively configured to digitally convert only the normal result of measurement and not the abnormal results of measurement.

In this case, an image associated with an abnormal result of measurement necessary for analysis of defects is transmitted in form of an analog signal with a high image quality to the host computer 10. On the other hand, an image associated with a normal result of measurement is digitally converted, and transmitted with a small data volume to the host computer 10.

Alternatively, when the judgment procedure is added, the semiconductor processing device 20 may be configured to transmit only an abnormal result of measurement and an image data associated with the abnormal result of measurement to the host computer 10.

In this case, abnormal results of measurement, job information and image data that are necessary for analysis of defects can be exclusively transmitted to the host computer 10. That is, the conversion procedure and transmission procedure, which are not necessary for analysis of defects, are omitted. Therefore, throughput of the semiconductor processing device 20 is further enhanced.

Figure 7:
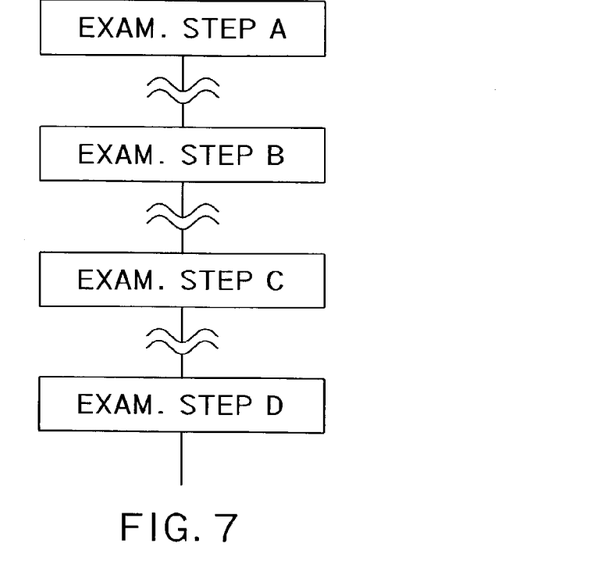
FIG. 7 is a diagram that shows an embodiment configured to change the data volume of image data for each step.

FIG. 7 is a diagram that shows an embodiment configured to change the data volume of image data for each step.

For example, in individual inspection steps A, B, C and D, the method of managing the semiconductor processing shown in FIG. 5 is carried out. In the inspection steps A, B, C and D, if the result of the measurement is good, the image is digitally converted to image data with a relatively small data volume. That is, selection information in each of the inspection steps A, B, C and D is determined to select an image-quality code using a smaller value of data volume. The selection information is set by an operator of the host computer 10.

As a result, the data volume of the image data is reduced, and the time for input, output, etc. of the image data can be shortened. Thus the time needed for the inspection steps is shortened.

However, assume that results of measurement show more defects than usual in the inspection step C. In this case, in order to make image data with a high image quality only the inspection step C, the selection information is modified to select another image-quality code for a larger data volume than usual.

As a result, while the throughput is maintained in the inspection step A, B and C, the image in the inspection step C is converted to image data of a high image quality using a relatively large data volume. Alternatively, the image in the inspection step C may be maintained in the form of analog signals without conversion. Since the image data in the inspection step C is a high image quality data, it is useful for reducing the time for analysis of defects.

Figure 8:
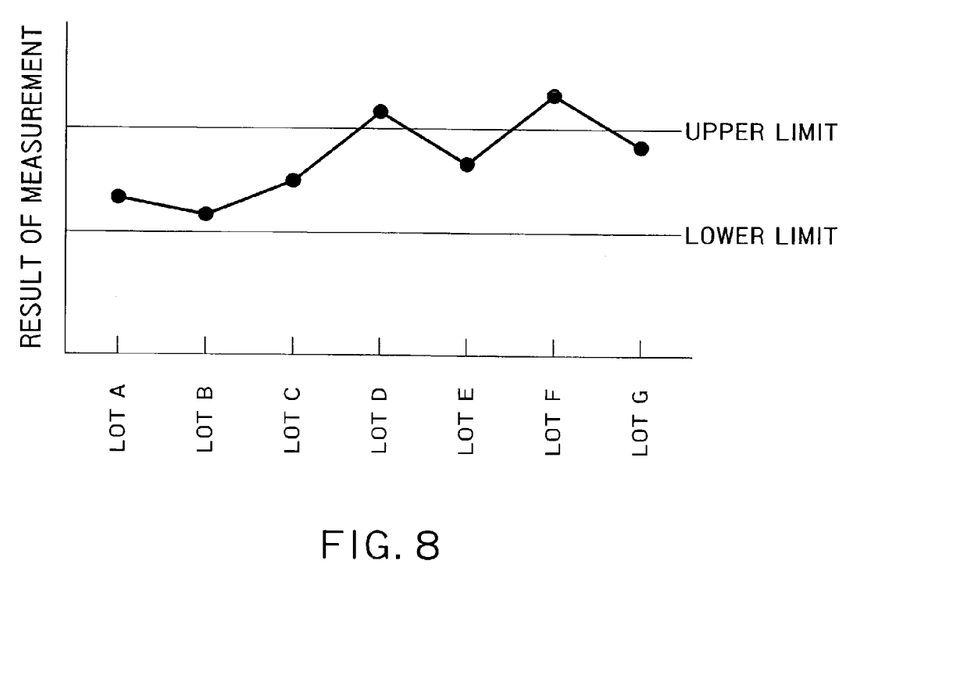
FIG. 8 is a diagram that shows an embodiment configured to change the data volume of image data for each lot.

FIG. 8 is a diagram that shows an embodiment configured to change the data volume of image data for each lot.

For example, in each lot A, B, C, D, E, F or G, the method of managing the semiconductor processing shown in FIG. 6 is carried out. Results of measurement of the lots A, B, C, E, and G are within a predetermined specification. In the judgment procedure (S615 in FIG. 6), therefore, the results of measurement satisfy a predetermined condition. That is, results of judgment of the lost A, B, C, E and G are normal results of judgment. Therefore, images of the lots A, B, C, E and G are converted to image data using a relatively small data volume (S616a).

As a result, data volumes of the image data are reduced, and the time for input or output, for example, of image data is shortened.

On the other hand, results of measurement of the lots D and F are out of the specification. Therefore, in the judgment procedure (S615), these results of judgment do not satisfy the predetermined condition. That is, results of judgment of the lots D and F are abnormal results of judgment. Therefore, images of the lots D and F are converted to image data using a relatively larger data volume (S616b). Alternatively, the images of the lots E and F are maintained in the form of analog signals without conversion. Since the image data in the inspection steps D and F are high image quality data, analysis of defects of the lots D and F is easier.

Figure 9:
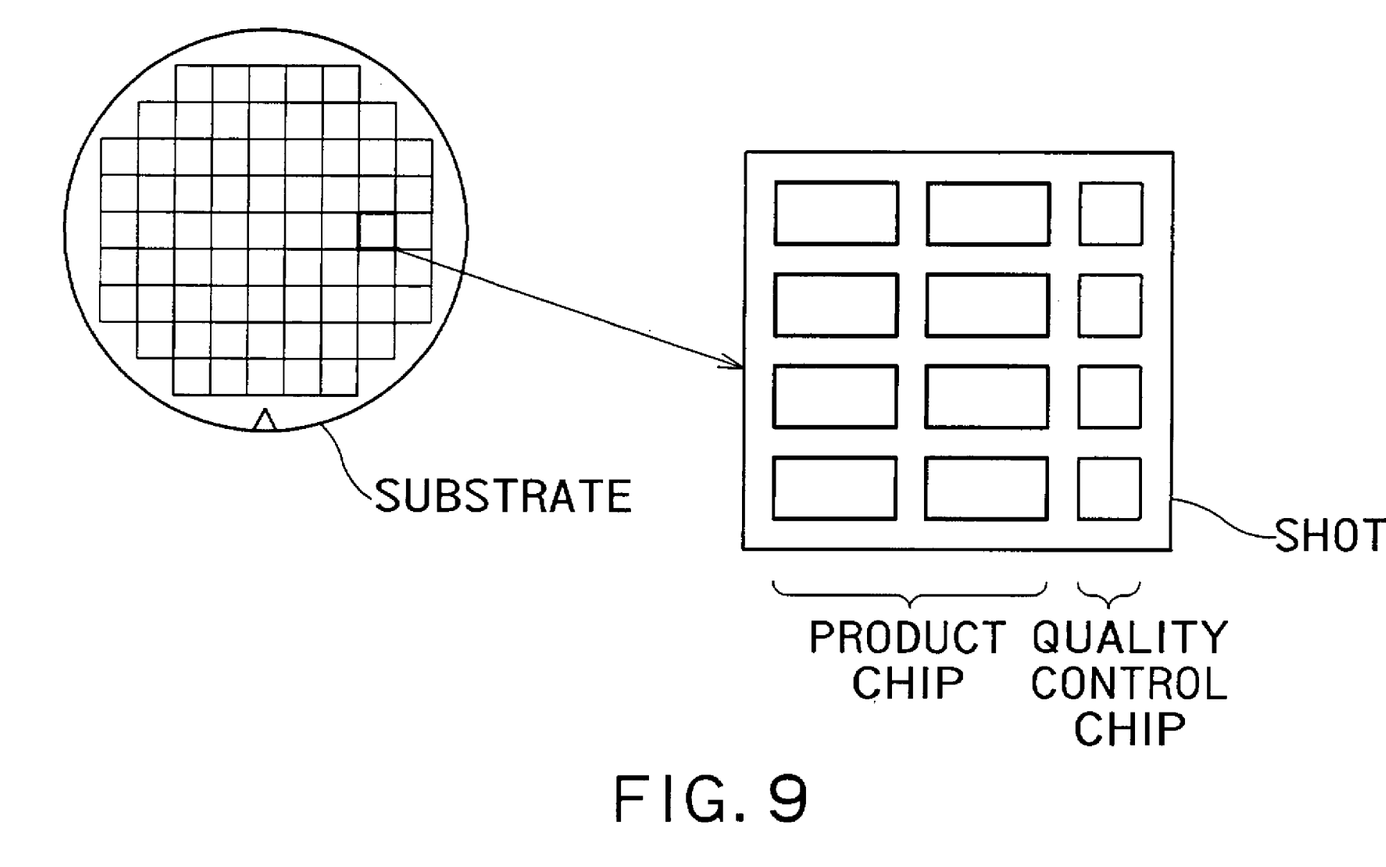
FIG. 9 is a diagram that shows an embodiment configured to change the data volume of image data in each chip at a predetermined location in a shot of a projection aligner.

FIG. 9 is a diagram that shows an embodiment configured to change the data volume of image data in each chip at a predetermined location in a shot of a projection aligner. In this embodiment, one shot on the semiconductor substrate includes product chips for products and quality control chips for quality control.

The semiconductor processing device 20 digitally converts an image upon measurement of a product chip to high image quality data using a relatively large data volume. If the product chip is defective, then the high image quality data is useful for reducing the time for analysis of defects. The semiconductor processing device 20 converts an image upon measurement of a quality control chip to low image quality data of a relatively smaller data volume. Therefore, the data volume transmitted from the semiconductor processing device 20 to the host computer 10 is reduced, and the throughput of the semiconductor processing device 20 is improved.

Figure 10A:
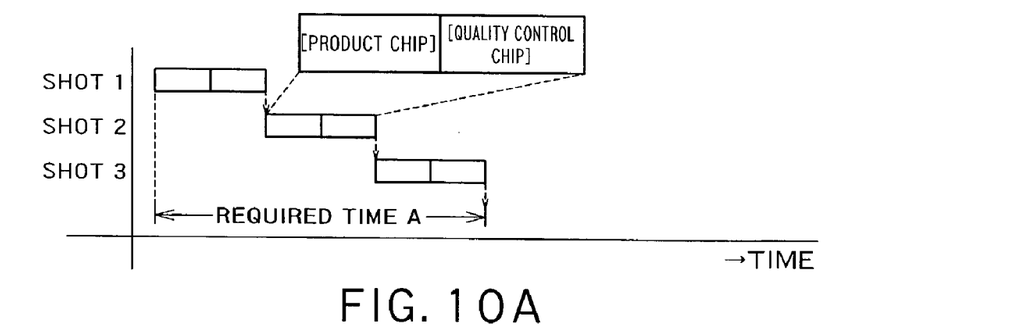
FIG. 10A is a diagram that shows durations of transmission time for transmitting image data from a semiconductor processing device to a host computer.
Figure 10B:
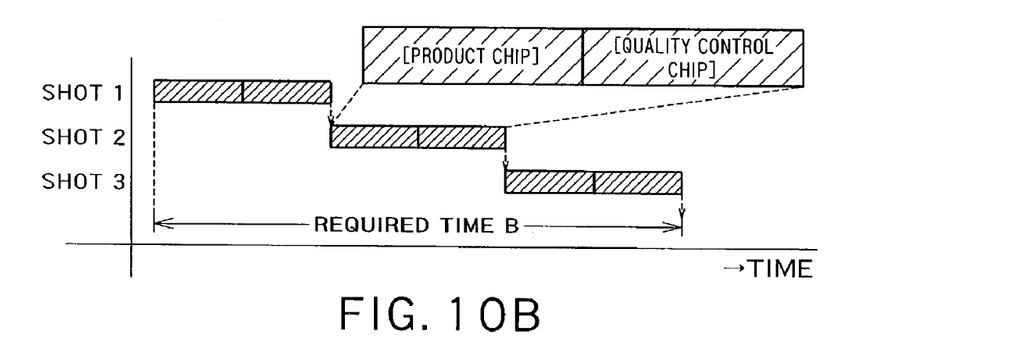
FIG. 10B is a diagram that shows durations of transmission time for transmitting image data from the semiconductor processing device to the host computer.
Figure 10C:
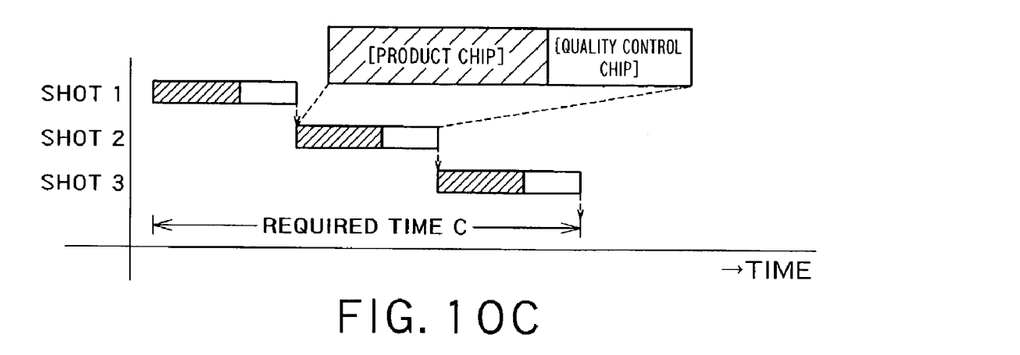
FIG. 10C is a diagram that shows durations of transmission time for transmitting image data from the semiconductor processing device to the host computer.

FIGS. 10A through 10C are diagrams that show durations of transmission time for transmitting image data from a semiconductor processing device 20 to a host computer 10. Transmission time of a product chip and transmission time of a quality control chip are distinguished for each exposure shot of the projection aligner. FIGS. 10A, 10B ad 10C each show the time for transmitting image data upon measuring chips in three exposure shots.

FIGS. 10A and 10B show the time required for transmitting image data by a conventional method of managing semiconductor processing. In FIG. 10A, both an image of a product chip and an image of a quality control chip are digitally converted to image data with a small data volume. Therefore, the time A required for transmission of the image data is short. However, the image qualities of the images reproduced from the image data of the product chip and the image data of the quality control chip are bad. That is, both the image data of the product chip and the image data of the quality control chip are low image quality data. As a result, if the product chip is defective, it may be difficult to use the image data for analysis of defects.

In FIG. 10B, both the image of the product chip and the image of the quality control chip are digitally converted to image data with a large data volume. That is, both the image data of the product chip and the image data of the quality control chip are high image quality data. Therefore, when the product chip is defective, the image data is useful for reducing the time for analysis of defects.

However, the time B required for transmission of the image data is relatively long, and the throughput of the semiconductor processing device 20 degrades.

FIG. 10C shows durations of transmission time for transmitting image data according to the embodiment of the invention shown in FIG. 9. In FIG. 10C, the image of the product chip and the image of the quality control chip are digitally converted to image data different from each other in data volume. For example, the image of the product chip is digitally converted to image data of a larger data volume, whereas the image data of the quality control chip is digitally converted to image data of a smaller data volume. That is, the image data of the product chip is high image quality data, whereas the image data of the quality control chip is a low image quality data.

Therefore, if the product chip is defective, then the image data is useful for reducing the time for analysis of defects. On the other hand, the time C required for transmission of the image data in the product chip is shorter than the time B for transmission of the image data in FIG. 10B.

Usually, there are a number of points to be measured in a semiconductor substrate. Especially in recent years where semiconductor elements are progressively miniaturized, the number of chips formed on a semiconductor substrate is increasing, and the points to be measured are increasing accordingly. Therefore, the effect of reducing the time B of FIG. 10B the time C according to the embodiment is significant.

In the specification, the term "image" is used to conceive "analog image file" as well. In the specification, the term "image data" is used to conceive "digital image file" as well. The semiconductor processing device 20 may be located inside the projection aligner or maybe an inspection apparatus independent from the projection aligner.

The semiconductor processing device, semiconductor processing system and method of managing semiconductor processing according to the invention can digitally convert individual images to image data files that are different from each other in volume or file format. As a result, the trade-off relationship between the time for analysis of defects and the throughput time of the semiconductor processing device can be removed.

What is claimed is:

1. A semiconductor processing device comprising:
a processing section to process a semiconductor substrate in accordance with job information which is used to process the semiconductor substrate;
an imaging section to take an image of a processed portion of the semiconductor substrate upon each time of processing by said processing section;
an image-processing section to convert any one and another of images of a plurality of the processes to image data which are different from each other in image-quality, and to associate a result of processing from the processing section, said job information and said image data with each other in each processing; and
an input/output section to output at least the result of processing and the image data.

2. A semiconductor processing device according to claim 1, wherein the data volumes of the image data which are different from each other in image quality are different according to file formats of the image data.

3. A semiconductor processing device according to claim 1, wherein said image-processing section digitally converts any one of the images to high image quality data, and digitally converts another of images to low image quality data, said high image quality data having a relatively large data volume, said low image quality data having a relatively small data volume.

4. A semiconductor processing device according to claim 1 further comprising a storage section to store image-quality codes which contain information about data volumes of the image data,
wherein the input/output section introduces selection information from outside, said selection information being changeable as desired and determining which of the image-quality codes stored in the image-quality code storage section should be selected, and
wherein the image-processing section digitally converts each of the images to the image data according to one of the image-quality codes which is selected for the each of the images.

5. A semiconductor processing device according to claim 4, wherein each image-quality code further contains information in relation to the file format of the image data.

6. A semiconductor processing device according to claim 1, wherein the processing portion is a measure section which measures the line width of a pattern formed on the semiconductor substrate.

7. A semiconductor processing system comprising:
(a) a semiconductor processing device comprising:
a processing section to process a semiconductor substrate in accordance with job information which is used to process the semiconductor substrate;
an imaging section to take an image of a processed portion of the semiconductor substrate upon each time of processing by said processing section;
an image-processing section to convert any one and another of images of a plurality of the processes to image data which are different from each other in image quality, and to associate a result of processing from the processing section, said job information and said image data with each other in each processing; and
an input/output section capable of outputting at least the result of processing and the image data, and
(b) a host computer being connected to the semiconductor processing device to input and store at least the result of processing and the image data which are output from the input/output section.

8. A semiconductor processing system according to claim 7 further comprising a storage section to store image-quality codes which contain information about data volumes of the image data,
wherein the host computer has selection information which is changeable as desired, said selection information determining which of the image-quality codes stored in the image-quality code storage section should be selected,
wherein the input/output section introduces the selection information from the host computer, and
wherein the image-processing section digitally converts each of the images to the image data according to one of the image-quality codes which is selected for the each of the images.

9. A semiconductor processing management method for a semiconductor processing device, which includes a processing section to process a semiconductor substrate, an imaging section to take an image of the semiconductor substrate upon processing by the processing section, and an image-processing section to process the image, comprising:

processing the semiconductor substrate according to job information which is prepared for processing the semiconductor substrate;
taking an image of the semiconductor substrate upon each time of processing by the processing section;
converting any and another of images of a plurality of the processes to image data which are different from each other in image quality;
associating the result of processing from the processing section, the job information and the image data with each other; and
externally outputting at least the result of processing and the image data.

10. A semiconductor processing management method according to claim 9 further comprising:
preparing an image conversion recipe after taking the image, said image conversion recipe having an arrangement of image-quality codes which contain information about the image-quality of the image data.

11. A semiconductor processing management method according to claim 9, wherein the images are converted to image data different in the data volumes during said conversion, the data volumes of the image data being different according to the file format of the image data.

12. A semiconductor processing management method according to claim 9, wherein digitally converting some of the images to high image quality data which has a relatively large data volume, and digitally converting the other images to low image quality data which has a relatively small data volume, during said conversion.

13. A semiconductor processing management method according to claim 9, wherein the semiconductor processing device stores image-quality codes which contain information about the data volume of the image data,
wherein inputting selection information from an exterior host computer prior to said conversion, said selection information being changeable as desired and determining which of the image-quality codes stored in the image-quality code storage section should be selected,
wherein digitally converting each of the images to the image data according to one of the image-quality codes during said conversion, said one of the image-quality codes being selected for the each of the images, and
wherein, outputting at least the result of measurement and the image data to the host computer during said externally outputting, and storing the image information in the computer, said host computer being connected to the semiconductor processing device.

14. A semiconductor processing management method according to claim 13, wherein forming an image conversion recipe after said inputting, said image conversion recipe having an arrangement of the image-quality codes according to the selection information.

15. A semiconductor processing management method according to claim 9, wherein, during said conversion, digitally converting an image taken in one of manufacturing processes of the semiconductor, in which the results of processing tend to dissatisfy a predetermined condition, to high image quality data which has a relatively large data volume, and
digitally converting an image taken in another of manufacturing processes of the semiconductor, in which the results of processing tend to satisfy the predetermined condition, to low image quality data which has a relatively small data volume.

16. A semiconductor processing management method according to claim 9, wherein digitally converting the images to high image quality data during said conversion in case of the result of processing is an abnormal result of processing which dissatisfies a predetermined condition, said high image quality data having a relatively large data volume digitally converting the image to low image quality data during said conversion in case of the result of processing is an normal result of processing which satisfies a predetermined condition, said low image quality data having a relatively small data volume.

17. A semiconductor processing management method according to claim 9, wherein digitally converting images of product chips, which are manufactured as a product, to high image quality data of a relatively large data volume during said conversion, digitally converting images of quality-control chips, which control the quality of products, to low image quality data of a relative small data volume during said conversion.

18. A semiconductor processing management method for a semiconductor processing device, which includes a processing section to process a semiconductor substrate, an imaging section to take an image of the semiconductor substrate upon processing by the processing section, and an image-processing section to process the image, comprising:

processing the semiconductor substrate according to job information which is prepared for processing the semiconductor substrate;

taking an image of the semiconductor substrate upon each time of processing by the processing section;

digitally converting at least any one of images of a plurality of the processes to image data different in data volume, and not converting another of the images to image data;

associating the result of processing from the processing section, the job information and the image data with each other; and externally outputting at least the result of processing and the image data.

\* \* \* \* \*